US011653938B2

United States Patent
Siegler

(10) Patent No.: US 11,653,938 B2
(45) Date of Patent: May 23, 2023

(54) PATIENT-SPECIFIC TEMPLATE FOR TOTAL ANKLE REPLACEMENT

(71) Applicant: Sorin Siegler, Narberth, PA (US)

(72) Inventor: Sorin Siegler, Narberth, PA (US)

(73) Assignee: DREXEL UNIVERSITY, Philadelphia, PA (US)

( * ) Notice: Subject to any disclaimer, the term of this patent is extended or adjusted under 35 U.S.C. 154(b) by 655 days.

(21) Appl. No.: 16/563,210

(22) Filed: Sep. 6, 2019

(65) Prior Publication Data

US 2020/0085452 A1 Mar. 19, 2020

Related U.S. Application Data

(60) Provisional application No. 62/731,223, filed on Sep. 14, 2018.

(51) Int. Cl.
*A61B 17/17* (2006.01)
*A61B 17/15* (2006.01)
*A61B 34/10* (2016.01)
*A61F 2/46* (2006.01)

(52) U.S. Cl.
CPC .......... *A61B 17/1775* (2016.11); *A61B 17/15* (2013.01); *A61B 17/1703* (2013.01); *A61B 34/10* (2016.02); *A61F 2/4606* (2013.01); *A61B 2034/108* (2016.02)

(58) Field of Classification Search
CPC ..... A61B 17/15; A61B 17/1775; A61B 34/10; A61B 2034/102; A61B 2034/105; A61B 2034/108; A61B 2017/568; A61B 2090/3614; A61F 2/4606
See application file for complete search history.

(56) References Cited

U.S. PATENT DOCUMENTS

| 6,875,222 | B2 * | 4/2005 | Long | A61B 17/142 606/178 |
| 8,337,503 | B2 | 12/2012 | Lian | |
| 9,017,334 | B2 | 4/2015 | Carroll et al. | |
| 9,237,950 | B2 | 1/2016 | Hensley et al. | |
| 9,603,711 | B2 | 3/2017 | Bojarski et al. | |
| 2004/0039394 | A1 * | 2/2004 | Conti | A61B 17/15 606/87 |
| 2010/0217338 | A1 * | 8/2010 | Carroll | B29C 64/386 606/86 R |
| 2010/0318088 | A1 * | 12/2010 | Warne | A61B 17/15 606/87 |
| 2012/0130434 | A1 * | 5/2012 | Stemniski | A61B 17/1775 606/86 R |
| 2012/0221008 | A1 | 8/2012 | Carroll et al. | |

(Continued)

FOREIGN PATENT DOCUMENTS

WO WO-2012125319 A1 * 9/2012 ............. A61B 17/15

*Primary Examiner* — Anu Ramana
(74) *Attorney, Agent, or Firm* — Mendelsohn Dunleavy, P.C.

(57) ABSTRACT

An alignment guide for total ankle replacement surgery and a method of creating and using the alignment guide. The alignment guide has a surface that interfaces with a corresponding surface of a superior aspect a talus of a patient, and as second surface portion that interfaces with a corresponding distal surface of a section of a tibia of the patient. When the alignment guide is in position, it maintains the ankle of the patient in a preselected position.

14 Claims, 11 Drawing Sheets

(56) References Cited

U.S. PATENT DOCUMENTS

2014/0066720 A1\* 3/2014 Wilkinson ............. A61B 17/02
606/88
2016/0008139 A1 1/2016 Siegler et al.

\* cited by examiner

PATIENT-SPECIFIC TEMPLATE FOR TOTAL ANKLE REPLACEMENT

CROSS-REFERENCE TO RELATED APPLICATIONS

This application claims the benefit of U.S. provisional application No. 62/731,223, filed on Sep. 14, 2018, the entire disclosure of which is hereby incorporated by reference herein.

BACKGROUND OF THE INVENTION

Many recent advances in the field of total ankle replacement (TAR) have been made which have enabled a higher success rate for this procedure. However, there are aspects of the process that can be improved to offer better outcomes for the patient.

During total joint replacement surgery the ends of the bones are resected to remove at least portions of the surfaces of the joint that have been damaged by injury or disease. A prosthesis is then applied on the end of each bone, and a spacer is located between the prostheses to provide the most natural joint motion and correct spacing between the bones.

The ankle of each patient, as well as each ankle on a single patient has its own unique anatomical and functional characteristics, which are influenced by the person's anatomy, or through use and disease over time. As such, each patient requires bone resection that is specifically tailored to the particular needs of that patient. For the joint function after TAR to be optimal, the bone resection must be accurate so that the prostheses are placed in the proper alignment and orientation.

Most existing Total Ankle Replacement (TAR) systems use complex, time consuming and often subjective alignment guides for preparing the necessary cuts, holes, etc. for implantation of the TAR components. Most such procedures require identification of the long axis of the tibia and then maintaining the plantar aspect of the foot perpendicular to this axis when cuts and holes are made. This alignment is referred to as a so-called "neutral alignment." Much of this alignment is done "by eye" resulting in misalignments and frequent failures due to misalignment of the TAR components. Additionally, the ankle joint is unstable and is difficult to place into the same alignment during second or subsequent alignment attempts, resulting in components that do not fit as precisely as they should when used as part of the TAR system.

Several attempts to use imaging technology to produce surgical guides for use with various joint replacement systems have been made. U.S. Patent Application Publication No. 2010/0217338 discloses a resection guide locator that is complementary to the surface of the bone to be resected. However, this resection guide locator does not address the alignment of two or more bones in a joint to ensure proper placement of an implant once the resection is complete.

U.S. Pat. No. 9,017,334 discloses a surgical instrument including a resection guide that has a surface that is complementary to the surface of the bone to be resected. The surface topography causes the guide to be fixed at a certain location on the bone. After the guide is fixed in place, a mounting guide for the resection device is attached to the resection guide, and a portion of the bone is resected. Although the placement of the resection devices is taught by this patent, maintaining the proper alignment between the bones in a joint to ensure proper alignment of an implant is not addressed.

U.S. Patent Application Publication No. 2012/0221008 teaches a system for total joint replacement surgery. The system of this disclosure has two parts. When used for total ankle replacement, the device comprises a tibial resection guide mount and a separate talar resection guide mount. The two guide mounts are used to resect the portions of each respective bone, but do not appear to be used to ensure the alignment of the bones in a preselected position throughout the joint replacement procedure.

U.S. Pat. No. 8,337,503 discloses cutting guides and instruments for use in total ankle replacement. The guides include a tibial component and a separate talar component. The two components are specifically designed to be separate pieces so that cuts to the bones of the joint can be made without alignment of the bones relative to each other.

U.S. Pat. No. 9,603,711 teaches patient-specific orthopedic implants, but does not address total ankle replacement systems, or the alignment between the bones of the ankle during total ankle replacement surgery.

U.S. Pat. No. 9,237,950 discloses a method of manufacturing a joint implant based on imaging of a patient's bone and determining the porous structure of the bone at the layer exposed by cutting away the bone's surface. The implant is then made to include a patient-specific porous construct attached to the planar surface of the implant.

Although many advances have been made, what is needed is a patient-specific guide system for use during the TAR process that maintains neutral alignment of the tibia and talus so that correct resection of the bones is accomplished.

SUMMARY OF THE INVENTION

In one aspect, the present invention relates to an alignment guide for use in ankle replacement surgery. The alignment guide may include:

a. a talar component having a surface portion that interfaces with a corresponding surface of a superior aspect of at least a section of a talus body and/or talus neck of an ankle of a patient; and b. a tibial component attached to the talar component having a surface portion that interfaces with a corresponding distal surface of at least a section of a tibia of the ankle of the patient.

A combination of the talar component, and the tibial component is configured such that when the surface portion of the talar component is positioned in contact with the corresponding surface of the superior aspect of at least said section of the talus body and/or talus neck of the ankle of the patient, and the surface portion of the tibial component is positioned in contact with at the corresponding distal surface of at least said section of the tibia of the ankle of the patient, the ankle of the patient is positioned in a preselected position.

At least the surface portion of the talar component of the alignment guide may be made using image data of the surface of the superior aspect of at least said section of the talus body and/or talus neck of the ankle of the patient. At least the surface portion of the tibial component may be made using image data of the distal surface of at least said section of the tibia of the ankle of the patient.

The image data of each of the foregoing embodiments may be obtained with the patient's ankle in a preselected position.

In each of the foregoing embodiments, the talar component and the tibial component may be integral with one another. Alternatively, the alignment guide of each of the foregoing embodiments may include an attachment means for attaching the talar component to the tibial component. The image data may be used to configure the attachment means to ensure that the ankle of the patient is positioned in a preselected position when:
  i) the talar and tibial components are attached to each other by the attachment means,
  ii) the surface portion of the talar component is positioned in contact with the corresponding surface of the superior aspect of at least said section of the talus body and/or talus neck of the ankle of the patient, and
  iii) the surface portion of the tibial component is positioned in contact with the corresponding distal surface of at least said section of the tibia of the ankle of the patient.

The attachment means of the alignment guide may be a releasable attachment means or an adjustable attachment means.

The tibial component of the alignment guide of each of the foregoing embodiments may be configured to allow visualization of one or both of a part of the tibia and a space between the tibia and the talus, when the surface portion of the tibial component is positioned in contact with the corresponding distal surface of at least said section of the tibia. For example, the tibial component of the alignment guide may include a removable section that, upon removal, allows visualization of one or both of a part of the tibia and a space between the tibia and the talus, when the surface portion of the tibial component is positioned in contact with the corresponding distal surface of at least said section the tibia.

The alignment guide of each of the foregoing embodiments may further include wires, pins or screws for attaching the alignment guide to the tibia and to the talus.

At least one of the tibial component and the talar component of the alignment guide of each of the foregoing embodiments may further include at least one aperture therein which is configured for guiding a drill, saw, or burring instrument.

The alignment guide of each of the foregoing embodiments may further include a navicular and cuboid component attached to or integral with the talar component and having a surface that interfaces with a superior part of a section of a surface of the navicular bone and a section of a surface of a cuboid bone of the patient.

The alignment guide of each of the foregoing embodiments may further include means associated with at least one of the tibial component and the talar component for attaching one or more of a cutting, drilling and/or burring jig to the alignment guide.

In each of the foregoing embodiments of the alignment guide, the distal surface of the tibia may include a portion of any of the anterior surface of the tibia, the lateral surface of the tibia, the medial surface of the tibia or any combination thereof.

In each of the foregoing embodiments of the alignment guide, the distal surface of the tibia is preferably a portion or all of the anterior surface of the tibia.

In another aspect, the invention relates to a method of forming an alignment guide for ankle replacement surgery. The method may include steps of:
  a. obtaining image-based data of a patient's ankle in a preselected position;
  b. producing a computer-based model of at least a portion of the patient's ankle in a neutral position from the image-based data;
  c. creating a tibial component for the alignment guide using the computer-based model including forming a surface portion of the tibial component that interfaces with a distal surface of at least a section of a tibia of the ankle of the patient; and
  d. creating a talar component for the alignment guide using the 3D model including forming a surface portion of the talar component that interfaces with a corresponding surface of a superior aspect of at least a section of a talus body or talus neck of the ankle of the patient.

A combination of the tibial component and the talar component is configured such that when the surface portion of the talar component is positioned in contact with the corresponding surface of the superior aspect of at least said section of the talus body or talus neck of the ankle of the patient, and the surface portion of the tibial component is positioned in contact with the distal surface of at least said section of the tibia of the ankle of the patient, the ankle of the patient is positioned in the preselected position.

The step of creating at least one of the tibial component and the talar component in the foregoing method may further include providing one or more apertures in at least one of the tibial component and the talar component, which apertures are configured for guiding a drill, saw, or burring instrument.

Each of the foregoing methods may further include a step of providing wires, pins, or screws configured to hold the alignment guide in place on the ankle of the patient during use.

In each of the foregoing methods, the step of creating the tibial component may include configuring the tibial component to allow visualization of one or both of a part of the tibia and a space between the tibia and the talus, when the surface portion of the tibial component is positioned in contact with the corresponding distal surface of at least said section of the tibia. In one embodiment, the tibial component may include a removable section that, upon removal, allows visualization of one or both of a part of the tibia and a space between the tibia and the talus, when the surface portion of the tibial component is positioned in contact with the corresponding distal surface of at least said section of the tibia.

Each of the foregoing methods may further include a step of altering the image-based data prior to producing the 3D model or altering the 3D model, to correct for injured or diseased bone that is to be resected during the ankle replacement surgery.

Each of the foregoing methods may further include steps of creating a navicular and cuboid component having a surface portion that interfaces with a corresponding surface of a superior aspect of at least a section of navicular and cuboid bones of the ankle of the patient and securing the navicular and cuboid component to the talar component. The navicular and cuboid component may be integral with the talar component.

In each of the foregoing methods, the alignment guide may be configured such that the tibial component is adjustable or removable from the talar component after the alignment guide is positioned on the ankle of a patient for ankle replacement surgery.

In each of the foregoing methods, the distal surface of the tibia may include a portion of any of the anterior surface of the tibia, the lateral surface of the tibia, the medial surface of the tibia or any combination thereof.

In each of the foregoing methods, the distal surface of the tibia is preferably a portion or all of the anterior surface of the tibia.

A second method of the invention is a method for total ankle replacement in a patient using any of the embodiments of the alignment guide described above. This method includes steps of:

a. exposing the distal surface of at least said section of the tibia of the ankle of the patient;

b. exposing the surface of the superior aspect of the section of the talus body or talus neck of the patient;

c. positioning the surface portion of the tibial component against the exposed portion of the distal surface of at least the section of the tibia of the ankle of patient; and d. positioning the surface portion of the talar component against the exposed superior aspect of the section of the talar body and neck of the ankle of the patient.

The second method may further include a step of affixing the alignment guide to one or both of the tibia and talus of the ankle of the patient using wires, pins, or screws.

Each of the foregoing embodiments of the second method may further include steps of attaching a cutting, drilling or burring jig to the tibial component of the alignment guide; and resecting bone using the cutting, drilling, or burring jig.

Each of the foregoing embodiments of the second method may further include a step of removing a portion of the tibial component to allow visualization of one or both of a part of the tibia and a space between the tibia and the talus, when the surface portion of the tibial component is positioned in contact with the corresponding distal surface of at least said section of the tibia of the ankle of the patient.

Each of the foregoing embodiments of the second method may further include a step of creating recesses in the talus of the patient using a guide which forms part of the talar component.

Each of the foregoing embodiments of the second method may further include a step of securing an ankle replacement to the tibia and talus of the patient.

In each of the foregoing embodiments of the second method, the distal surface of the tibia may include a portion of any of the anterior surface of the tibia, the lateral surface of the tibia, the medial surface of the tibia or any combination thereof.

In each of the foregoing embodiments of the second method, the distal surface of the tibia is preferably a portion or all of the anterior surface of the tibia.

BRIEF DESCRIPTION OF THE FIGURES

FIG. 9A is a computer-generated image of a front view of the alignment guide of FIG. 6A having a removable cutting guide.

FIG. 9B is a perspective view of the alignment guide of FIG. 9A showing the cutting guide being removed.

FIG. 11A is a computer-generated image of a front view of the alignment guide of FIG. 6A having a removable alignment apparatus.

FIG. 11B is a side view of the alignment guide of FIG. 11A.

DETAILED DESCRIPTION OF EMBODIMENTS OF THE INVENTION

Figure 1:
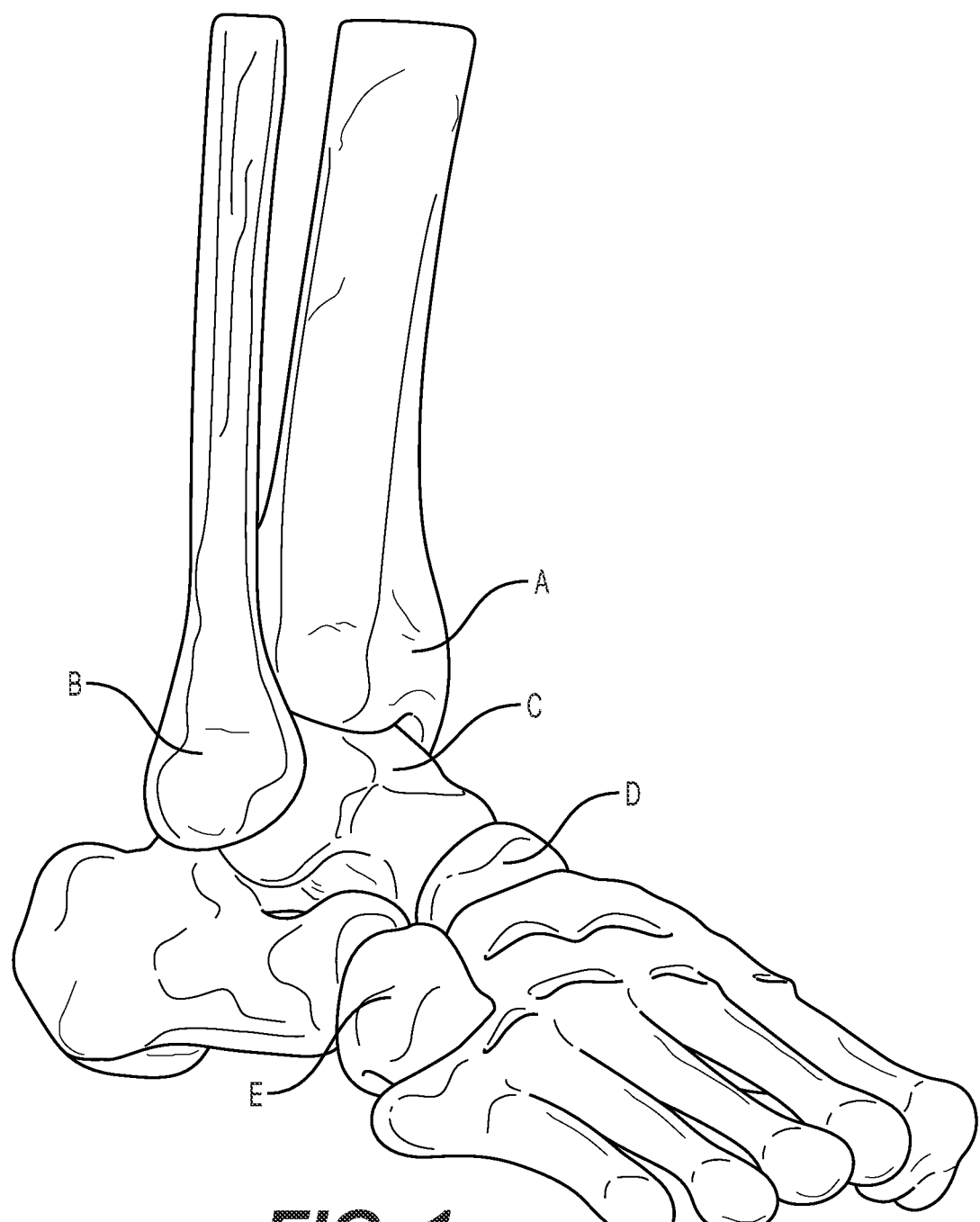
FIG. 1 is a perspective view of the bones of an ankle.

In one aspect, the present invention relates to an alignment guide for use in ankle replacement surgery. The alignment guide is designed to position the ankle of the patient in a preselected position for at least part or all of the ankle replacement procedure. In this manner essentially the best fit of the ankle replacement can be achieved for each patient.

The invention provides significant advantages in that the alignment guide can be customized to each patient. Thus, anatomical variations among the ankles of different patients can be taken into account in fabrication of the alignment guide to ensure the best fit of the ankle replacement for that particular patient.

In addition, many candidates for ankle replacement will have some damage to the bones of the ankle due to, for example, arthritis or other causes. It may be desirable to resect one or more bones of the patient's ankle to remove damaged bone and/or provide a suitable surface portion for attachment of the ankle replacement. The alignment guide of the present invention can also be customized for use with resected bone in order to ensure the best fit of the ankle replacement to the resected bone of the ankle of the patient.

Also, the alignment guide can obviate the need to use generic alignment guides to determine the location of bone resection necessary to place an implant in the desired location.

The alignment guide of the present invention may include:

a. a talar component having a surface portion that interfaces with a corresponding surface of a superior aspect of at least a section of a talus body or talus neck of an ankle of a patient; and b. a tibial component attached to the talar component having a surface portion that interfaces with a corresponding distal surface of at least a section of a tibia of the ankle of the patient.

A combination of the talar component, and the tibial component of the alignment guide of the present invention is configured such that when the surface portion of the talar component is positioned in contact with the corresponding surface of the superior aspect of at least said section of the talus body or talus neck of the ankle of the patient, and the surface portion of the tibial component is positioned in contact with at the corresponding distal surface of at least said section of the tibia of the ankle of the patient, the ankle of the patient is positioned in a preselected position.

For convenience, the talar component and tibial component are referred to as individual components of the alignment guide of the present invention, primarily for the purpose of describing the characteristics of the surface portions of these components. However, the tibial component and talar component may be integral with one another. The term "integral" as used herein includes not only a unitary or one-piece construction but also the formation of an integral structure from the components by, for example, fastening or welding or similar means for combining the components into an integral structure. Additionally, the talar and tibial components may be two separate components that can be used individually or may interact with one another using, for example, interfacing surfaces.

In other embodiments the talar and tibial components may be interconnected with one another by, for example, a suitable attachment means, to form the alignment guide. Suitable attachment means may include a releasable attachment means which would allow disengagement of one of the tibial and talar components from the other of the components. Such attachment means may include, for example, a snap fit or friction fit, screws, bolts, hooks, adhesives, wires such as kirshner wires, pins or any other similar means for attaching the components together.

Thus, a combination of the talar component and the tibial component encompasses both talar and tibial components that are integral with one another and talar and tibial components that are attached to one another via an attachment means as described above. The combination may also encompass separate talar and tibial components that are configured to interact with one another using, for example, complementary interfacing surfaces.

As used herein, "preselected position" refers to the position of the ankle that is selected as the position for ideal implant placement for a particular patient. Any suitable angle of the ankle joint may be used for this position, but it must be selected prior to creating the template. Often, the neutral position of the ankle is preferred for this purpose, but the preselected position may not always be the neutral position. For instance, in some cases it may be desirable for the preselected position to be offset from the neutral position. Preferably, this offset is small and may be up to 10 degrees in any direction and, more preferably, the offset is up to four degrees in any direction. The "preselected position" may also refer to the position that a patient's ankle is in when the patient is standing in an upright position, which may not always be the neutral position.

As used herein, the "neutral position" refers to the position of the ankle wherein the plantar aspect of the foot is positioned parallel to a flat surface and perpendicular to the longitudinal axis of the tibia. The neutral position of the ankle is typically the point in the range of motion of the ankle at which the ligaments and other non-muscular tissues around the ankle are required to provide the least amount of support.

As used herein, the term, "approximately" as used, for example, in the phrase, "approximately fits", means not exact. Thus, a surface portion that approximately fits another surface portion does not exactly fit. As a result, the distance between the surface portions may vary by up to 0.5 mm, or up to 0.25 mm, or up to 0.1

As used herein, the phrase, "interfaces with" refers to contact between two surfaces that ensures that the surfaces are retained in a static position relative to each other. For example, for a surface to interface with another surface the two surfaces may be in complete contact or there may be two or more points of contact between the two surfaces as long as sufficient points of contact are used to maintain a static position of the first surface relative to the position of the second surface.

As used herein, the term, "distal surface of the tibia" may include a portion of any of the anterior surface of the tibia, the lateral surface of the tibia, the medial surface of the tibia or any combination thereof.

The invention provides an alignment guide for aligning the tibia and talus of the patient's ankle in a preselected position for the ankle replacement surgery. A customized alignment guide is prepared for each patient. The customized alignment guide may be prepared using data about the patient's ankle. This data can be used to directly create the alignment guide or to first make a model of at least the relevant portions of the patient's tibia and talus and then subsequently making an alignment guide to fit the model.

The invention disclosed herein may employ image-based data of the patient's ankle obtained by computer tomography (CT), magnetic resonance imaging (MRI), etc. to produce the alignment guide or accurate computer-based models of the articulating bones of the ankle of the patient when located in a preselected position. FIG. 1 shows the bones of the ankle in a preselected position, which in this case is the neutral position.

The present invention primarily utilizes the surfaces of the tibia A, fibula B, and talus C bones of the ankle. Using a computer-based model created from image data obtained of a particular patient's ankle, a multi-bone template, or alignment guide is produced that accurately fits the front of the patient's ankle bones including the anterior part of the distal tibia, the superior aspect of the talus bone and neck and optionally the superior part of the navicular D and cuboid E bones. The alignment guide may be made, for example, by 3D printing, polymer molding, polymer etching, or other suitable manufacturing techniques known to persons skilled in the art.

Figure 4:
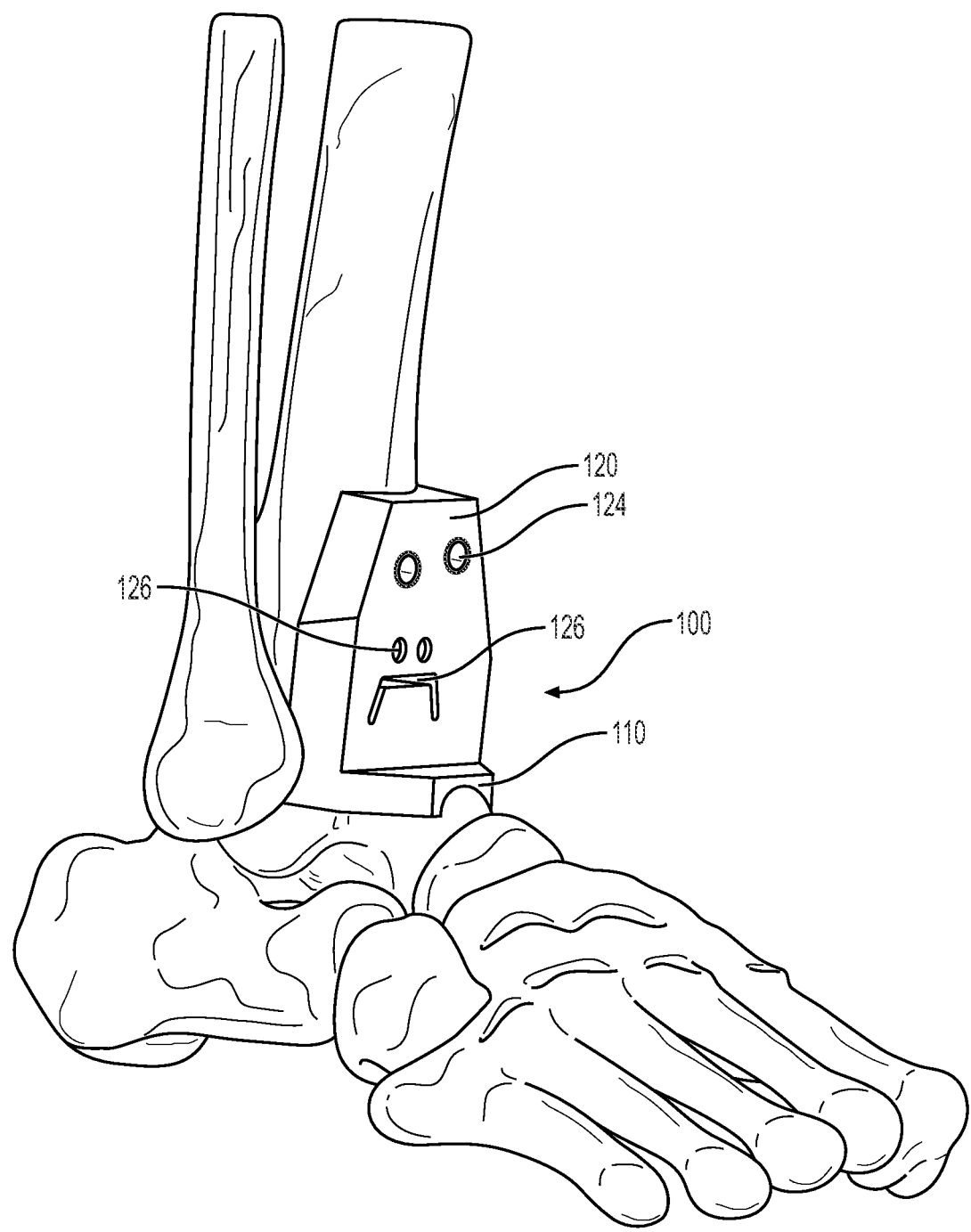
FIG. 4 is a computer-generated image of a perspective view from the lateral side of the ankle of the alignment guide of FIG. 2 in place on the bones of an ankle.
Figure 5:
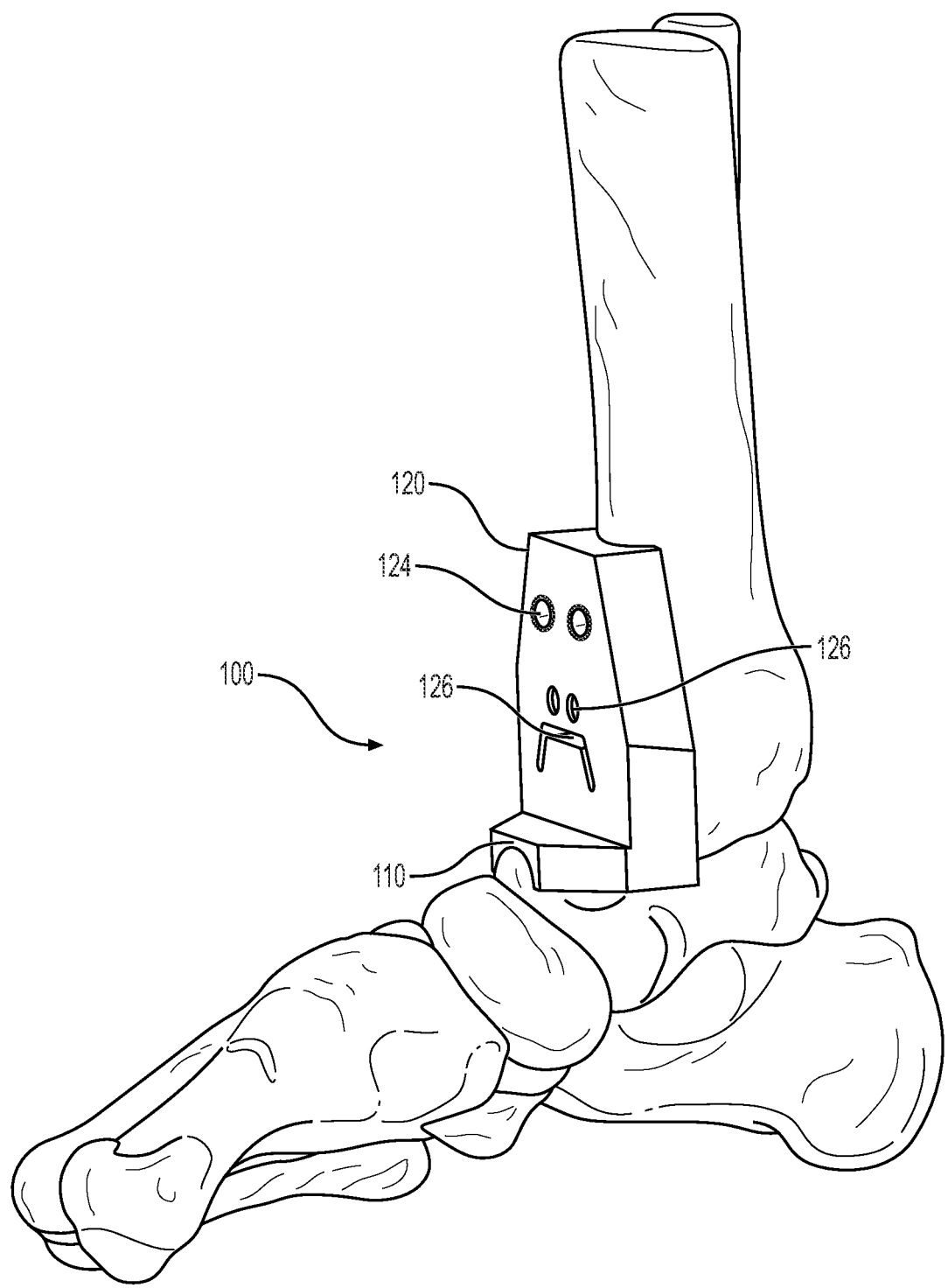
FIG. 5 is a computer-generated image of a perspective view from the medial side of the ankle of the alignment guide in place on the bones of an ankle shown in FIG. 4.

During the surgical preparation for TAR, the anterior part of the distal tibia, the superior aspect of the talus and possibly the superior part of the navicular and/or cuboid are surgically exposed. The alignment template is then fixed to the exposed parts of some or all of these bones of the ankle for the purpose of producing a close fit with the ankle bones that provides a rigid alignment of the ankle bones in the preselected position. FIGS. 4 and 5 show the alignment guide positioned against the tibia and talus bones to hold the ankle bones in the proper alignment position.

The template may be fixed to the bones via, for example, kirshner wires, pins, screws, or any other attachment devices known in the art to be used for securing surgical guides to bone surfaces. Additionally, the template may be attached to another device that is rigidly fixed to the bones via Kirshner wires, pins, screws, or other attachment devices known in the art. Depending on the specific TAR that is implanted, one or more cutting, drilling, and/or burring jigs can optionally be attached to the alignment guide to enable accurate fixation of the TAR components to the bones of the ankle while these bones are rigidly maintained in the neutral alignment position. These cutting, drilling and/or burring jigs may be also be customized to fit the patient's specific anatomy. In some cases the cutting, drilling and/or burring jigs may be a part of the guide itself, wherein the guide contains the holes, slots, or other features that accept and guide bone resection instruments, such as saws, burs, wires or drills.

The alignment guide may also optionally include a surgical guide or cut out feature specifically designed to ensure that a proper portion of one or more bones is resected during the procedure to ensure that the TAR closely fits in the space created by the resection. In addition to the surgical guides, various extensions can be attached to the template to verify proper alignment of the ankle bones relative to one or more other portions of the patient's anatomy. In this manner, for example, alignment relative to the long axis of the tibia or relative to the inter-malleolar axis can be verified, as desired.

Figure 2:
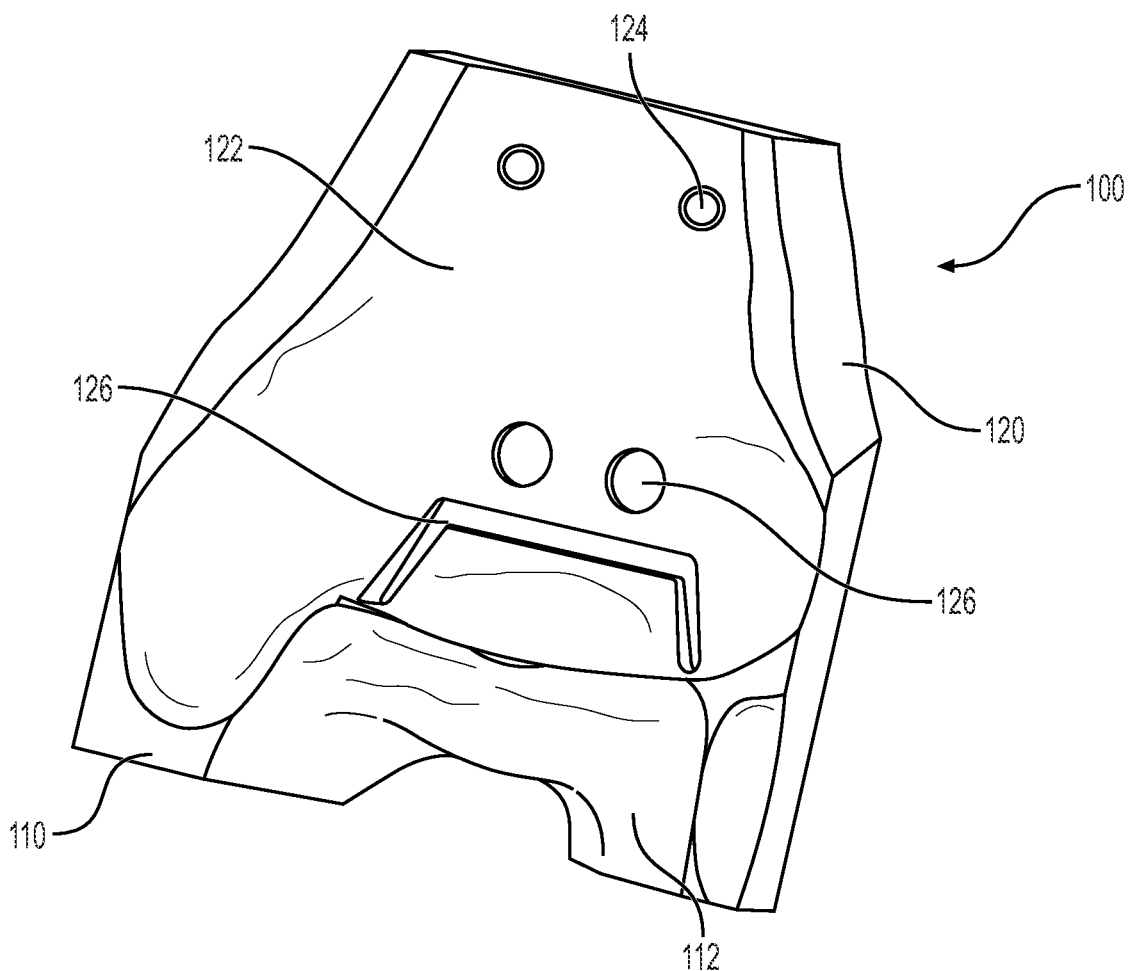
FIG. 2 is a computer-generated image of a perspective view of an alignment guide according to an embodiment of the present invention.
Figure 3:
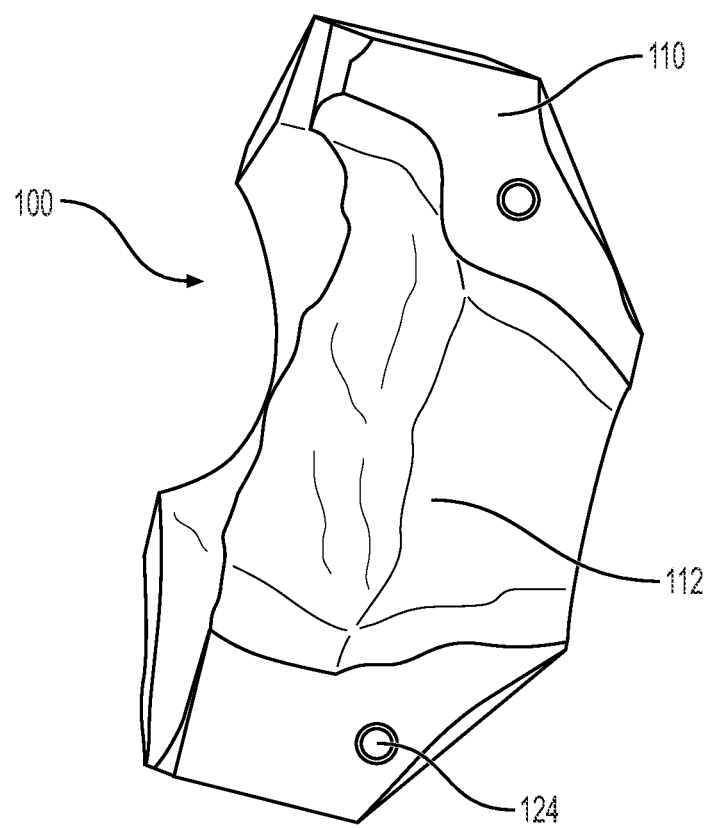
FIG. 3 is a computer-generated image of a perspective view of the bottom of the alignment guide of FIG. 2.

Two different perspective views of an alignment guide in accordance with the present invention are shown in FIGS. 2 and 3. As seen in FIG. 2, the alignment guide 100 includes a talar component 110 and a tibial component 120. The talar component 110 has a surface portion 112 that is configured to interface with a corresponding surface of a superior aspect of at least a section of a talus body or talus neck of an ankle of a patient. The tibial component 120 has a surface portion 122 that is configured to interface with a distal surface of at least a section of a tibia of the ankle of a patient. At the interface, the surface portion 112 of the talar component and the surface portion 122 of the tibial component preferably approximately or exactly fit with the corresponding talus body or neck, and the distal surface of a section of a tibia, respectively.

The surface portions 112, 122 of the talar and the tibial components 110, 120 may be formed by using a computer-based model, such as a 3D model, or two or more 2D pictures of the relevant sections of the patient's tibia and talus. The computer-based model may be created from image-based data obtained from a MRI, CT, X-ray, and/or other imaging technology by scanning of a patient's ankle while the ankle is positioned in the neutral position, or other preselected position. The positioning of the patient's ankle can be accomplished by having the patient stand upright during imaging, attaching a device to the patient's ankle to hold the joint in the correct position, or manipulating the data used to create the computer-based model to compensate for the bone position during data acquisition. The model may be a computer-generated model implemented by a processor and suitable computer equipment. From the computer-based model, suitable instructions can be generated for creating the alignment guide 100. The alignment guide can be created by printing, machining, or other known manufacturing techniques. Preferably, the alignment guide is created using a 3D printer using known algorithms for this purpose.

FIG. 3 shows a bottom perspective view of the alignment guide 100. This view shows the surface portion 112 of the talar component 110. The surface portion 112 of the talar component 110 is made to interface with the talus body as defined above, preferably by approximately or exactly fitting the corresponding surface of the superior aspect of at least a section of the talus body or talus neck, preferably using image data of the surface of the superior aspect of at least said section of the talus body or talus neck of the ankle of the patient. Similarly, the surface portion 122 of the tibial component 120 is made to interface with the tibia as defined above, by approximately or exactly fitting the corresponding surface of the distal surface of at least a section of the distal tibia of the ankle of the patient, preferably using image data of the corresponding surface of the distal surface of at least a section of the distal tibia of the ankle of the patient.

Preferably, an exact fit between a surface of the bone and the surface portion 112 or 122 of the talar or tibial component 110, 120 means that the sections of the surfaces of the talus and tibia touch the surface portions 112, 122, respectively, over at least 99% of the surface portion 112 or 122 of the tibial or talar components 110, 120. Although an exact fit may be desirable in many cases, there are circumstances that may require the use of an approximate fit between the surfaces. Additionally, in other circumstances only a few points of contact are possible between the surfaces, in which case, the interface between the surfaces only requires that the guide is held in a steady position with respect to the bones of the patient. The interface is based on the computer-based model created from the image data.

The alignment guide 100 is configured such that the location of the surface portion 112 of the talar component 110 and location of the surface portion 122 of the tibial component 120 correspond to the location of tibia and talus bones when the ankle of the patient is positioned in the preselected position, which is preferably the neutral position or within about 4 degrees in any direction starting from the neutral position. These locations of the surface of the talar component 110 and the surface of the tibial component 120 allow the alignment guide 100 to align the joint in the preselected position when the surfaces of the guide are positioned in contact with the respective surfaces of the bones.

FIGS. 4 and 5 show the alignment guide 100 fitted with the surface sections of the tibia and talus bones. The ankle as shown in in FIGS. 4 and 5 is in the neutral position. When the alignment guide 100 is properly fitted with the surface section of the tibia and talus bones, the ankle will necessarily be positioned in the neutral position due to the fact that the alignment guide 100 was constructed from the data obtained from the patient's ankle when positioned in the neutral position. By maintaining the ankle in neutral position during the ankle replacement procedure, accurate placement of the replacement joint components can be assured. Similarly, the ankle can be placed in any preselected position when the image data is obtained, and the alignment guide may be created from that data. In such cases, the ankle is maintained in this preselected position during the procedure.

Figure 6A:
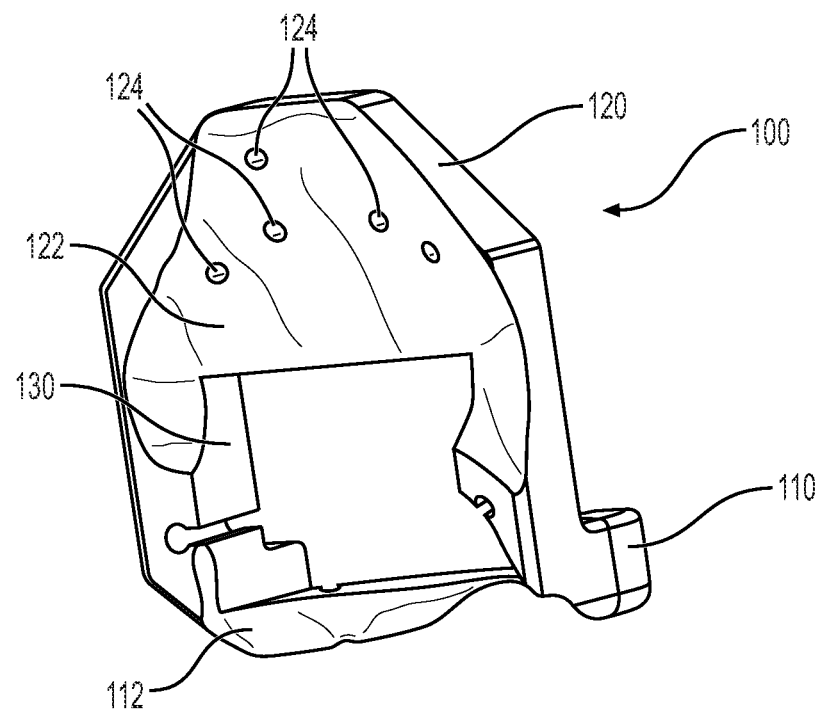
FIG. 6A is a computer-generated image of a perspective view of the alignment guide shown in FIG. 2 showing a portion removed according to an embodiment of the present invention
Figure 6B:
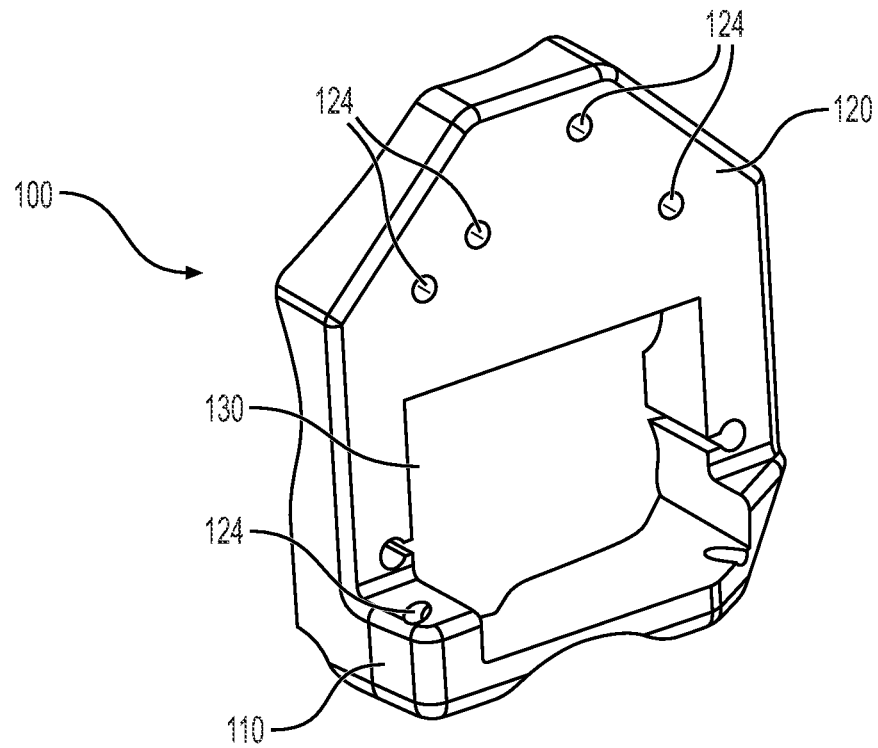
FIG. 6B is a computer-generated image of a perspective view of the front of the alignment guide shown in FIG. 6A.

Preferably, the alignment guide 100 is a single body wherein the talar and tibial components 110, 120 are integral. The tibial component 120 may be completely solid, but is preferably configured to allow visualization of one or both of a part of the tibia and a space between the tibia and the talus when the tibial component 120 is positioned on the patient's ankle for use. Visualization may be provided by use of a specific shape of the tibial component 120, by providing an opening in the tibial component 120 for viewing, by making a portion of the tibial component 120 of a transparent material or any combination thereof. FIGS. 6A and 6B show an alignment guide 100 having an opening 130 to allow for visualization of the bone through the tibial component 120. Additionally, an aperture or guide for a camera, fiber optic, or other visualization device, can be provided as part of the alignment guide 100 to facilitate visualization.

Alternatively, or in addition to the above visualization methods and apparatus, visualization may be provided through the use of a removable section in the tibial component 120. Upon removal of the removable section, visualization of one or both of a portion of a part of the tibia and the space between the tibia and the talus is possible when the surface portion 122 of the tibial component 120 is positioned in contact with the corresponding distal surface of at least a section of the tibia. By having a removable section, increased functionality can be realized while using the alignment guide 100. The removable section may be completely separable from the tibial component, or may be a piece that maintains connection, but can be adjusted so that it is moved to a position that allows for viewing and does not interfere with the procedure.

Figure 7A:
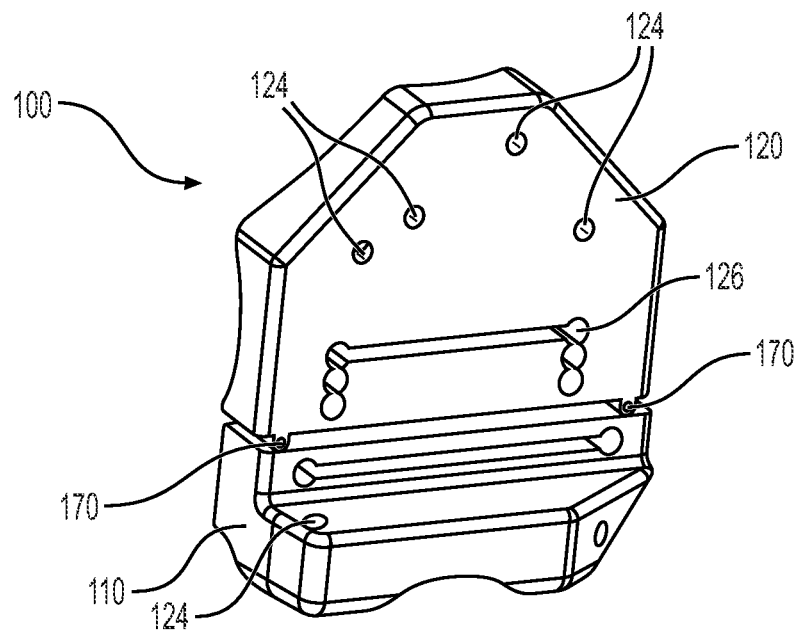
FIG. 7A is a computer-generated image of a perspective view of an alignment guide having an attachment means according to an embodiment of the invention.
Figure 7B:
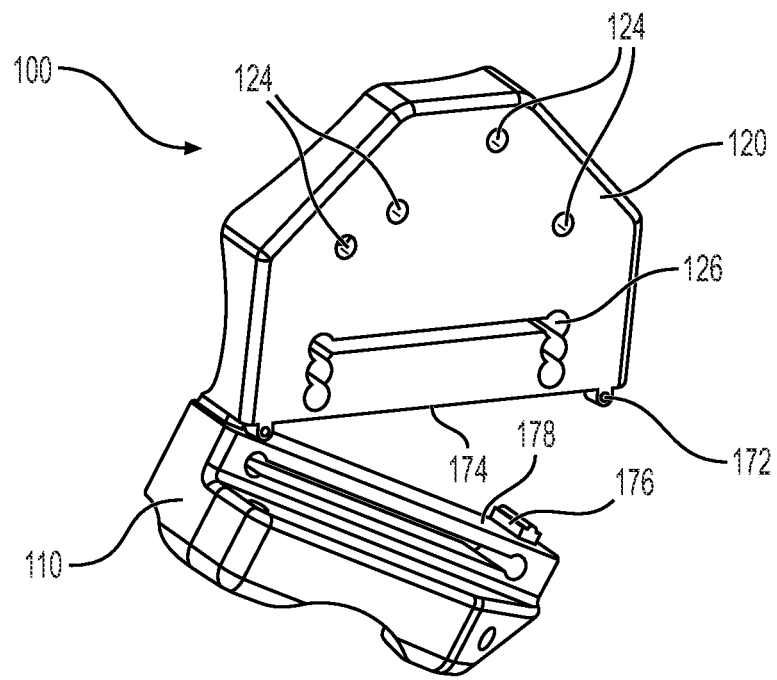
FIG. 7B is a view of the alignment guide shown in FIG. 7A showing how the parts may be detached from one another.

In an alternative embodiment, the talar component 110 and the tibial component 120 may be two separate parts that are attached to each other through the use of an attachment means. An attachment means may be a screw and nut, a screw threaded into a hole in one of the components, clamping the components together, the use of an adhesive, such as glue or tape, or any other known method of securing two items to each other. The attachment means is configured to ensure that the talar component 110 and the tibial component 120 are secured to each other in such a fashion that they cannot be moved relative to each other to thereby provide rigid positioning of the ankle of the patient. The attachment means is also configured to ensure that when the alignment guide 100 is located in place on the ankle of the patient, the ankle of the patient is rigidly maintained in the preselected position. The attachment means may be adjustable in one or more planes to modify the relative location of the tibial and talar components of the alignment guide with respect to each other and/or the bones of the ankle, as shown in FIGS. 7A and 7B. FIG. 7A shows an alignment guide 100 having an attachment between the tibial component 120 and a talar component 110 that holds them in position relative to each other to maintain an ankle joint in or close to a neutral position, but in some cases another position may be more desired.

In one embodiment, the attachment means 170 shown in FIGS. 7A and 7B is a snap fit with two points of attachment having a friction fit between the tibal outer pieces 172 located at the front and back of the lower surface 174 of the tibial component and a talar inner piece 176 located on the upper surface 178 of the talar component and between the tibial outer pieces 172 such that there is a friction fit between the tibial outer pieces 172 and the talar inner piece 176 when they are in contact with each other. Such a friction fit may create a hinge joint between the talar component 110 and the tibial component 120. As shown in FIG. 7B, one of the two attachment points 170 having a snap fit may be disconnected, which allows rotation about the other hinge joint. Such motion allows for an adjustable position of the talar and tibial components 110 and 120 with respect to each other, if desired.

The attachment means may also made using the image data obtained from the ankle to help ensure that the ankle of the patient is held in a preselected position when the alignment guide 100 is located in place on the ankle of the patient. The attachment means may be a permanent or a releasable attachment. In the case of a releasable attachment, one of the talar and tibial components 110, 120 may be removed after location of the alignment guide 100 in place on the ankle of the patient while the other of the talar and tibial components 110, 120 remains in place on the patient's ankle.

Figure 8:
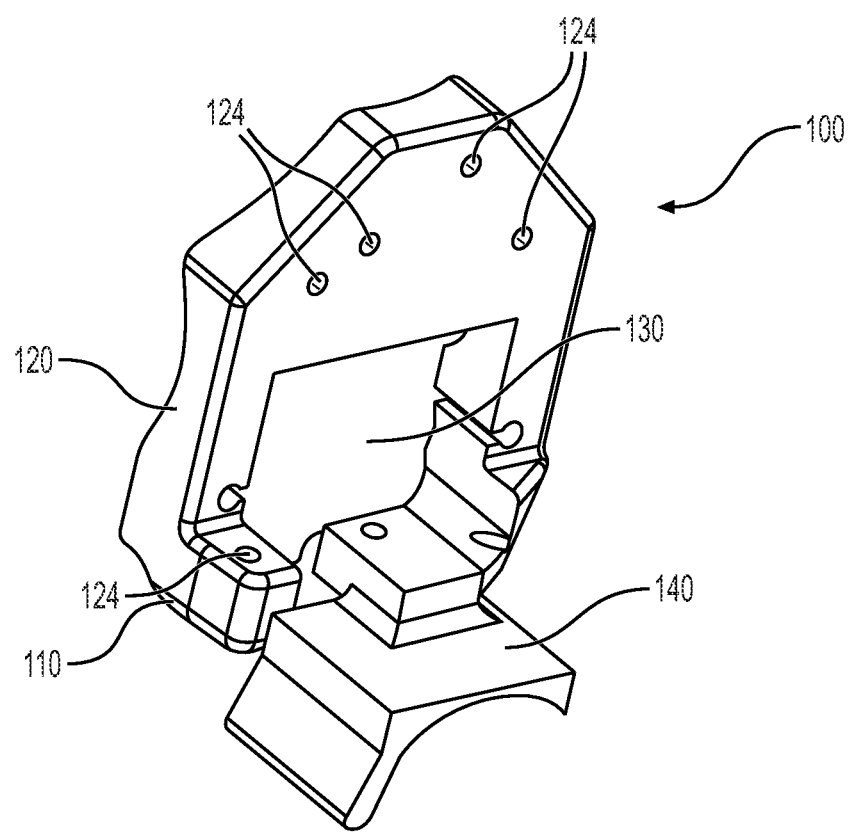
FIG. 8 is a computer-generated image of a perspective view of the alignment guide of FIG. 6A having a navicular and cuboid component.

In any of the foregoing embodiments of the alignment guide 100, a third component may also be included. The third component, if present, may be a navicular and cuboid component, as shown in FIG. 8. The navicular and cuboid component 140 is provided with a surface portion that interfaces with a corresponding surface of at least a section of the superior part of the navicular and cuboid bones of the patient's ankle. Preferably, this interface is achieved by approximately or exactly fitting with the corresponding surface of the navicular and cuboid bones. The navicular and cuboid component 140 may be integral with the alignment guide 100, with the talar component 110, or may be a separate piece that is attached to the talar component 110 using an attachment means, as shown in FIG. 8.

The alignment guide 100, once positioned on the patient's ankle as described above, is secured in place to one or more of the bones of the ankle through the use of wires, pins, screws, or other suitable securing devices that are known to persons skilled in the art. As such, the alignment guide 100 is preferably provided with fixation portions for such securing devices such as one or more openings 124 for the use of these securing devices to securely hold the alignment guide 100 in place on the patient's ankle. The figures show a particular configuration of openings 124 in the tibial component 120. However, openings 124 may be provided at any suitable location(s) in the alignment guide 100, including in one or more of the tibial component 120, the talar component 110, or the optional navicular and cuboid component. Additionally, it may be desirable to provide a plurality of securing points in one or more of the components to ensure that the alignment guide 100 is safely and tightly secured to the ankle of the patient, and that the ankle cannot move out of the preselected position.

The primary purpose of the alignment guide 100 is to securely and accurately maintain the patient's ankle in the preselected position during the procedure. However, the alignment guide may also provide a guide 126 for instruments that are used to resect or resurface the bone of the ankle of the patent. As such either or both of the tibial component 120 and the talar component 110 may include at least one guide 126 that many be in the form of a shaped aperture located in a desired position that can be used as the guide 126 to align a drill, saw, burring instrument, or any other suitable instrument used to remove, or resurface bone. Resurfacing of the bone may involve altering or reforming the surface of the bone. Either or both of the tibial component 120 and the talar component 110 of the alignment guide may also be provided with structure for attachment of one or more of a cutting, drilling, burring, or alignment jigs or apparatus. Such structure may include protrusions, or holes to which these jigs can be securely affixed in a position that ensures that instruments are properly positioned for use during the procedure. FIGS. 2, 4 and 5 show an embodiment of a guide 126 for facilitating resection of a portion of the tibia. The guide 126 as shown in the figures is an aperture having the shape of the top three sides of a trapezoid. When a saw, or other resection device is inserted through the aperture, it is aligned to remove the portion of the bottom of the tibia that corresponds to the replacement piece that will be inserted into the opening and affixed to the bone. Although a specific shape is shown for the resection guide, it is understood, that any shape that conforms to the implant being inserted into the joint can be used such that the implant is capable of fitting with, and being securely affixed to, the surface of the bone. The guide 126 portion of the alignment guide 100 can also be customized for each individual patient's ankle or implant to be used for that patient using data on the patient's ankle or implant.

Figure 9C:
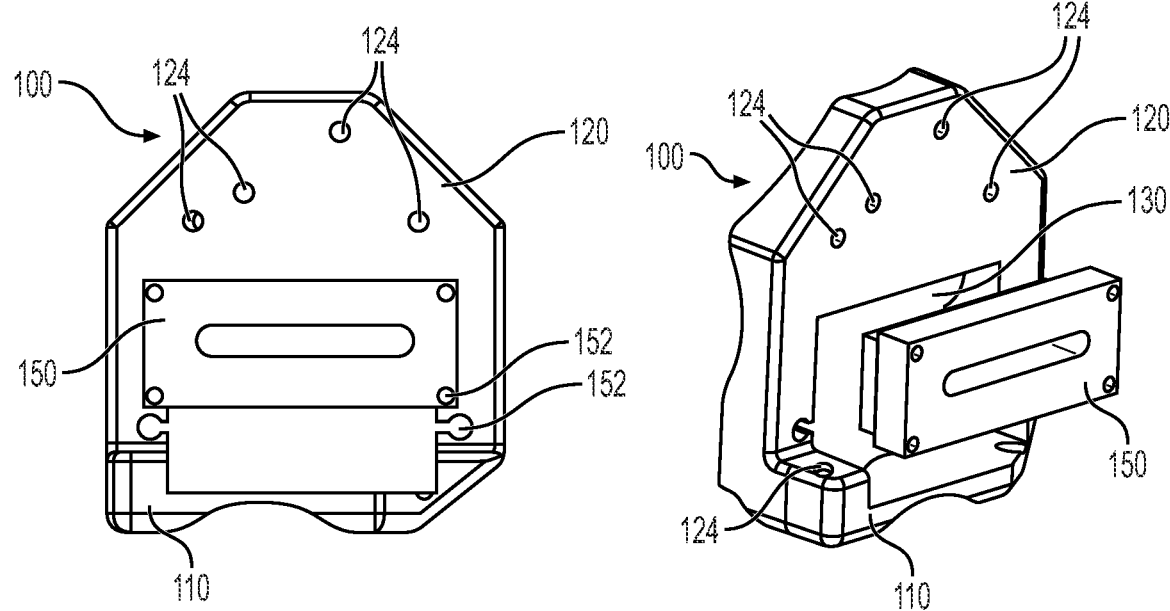
FIG. 9C is a perspective rear view of the alignment guide of FIG. 9A.
Figure 9C:
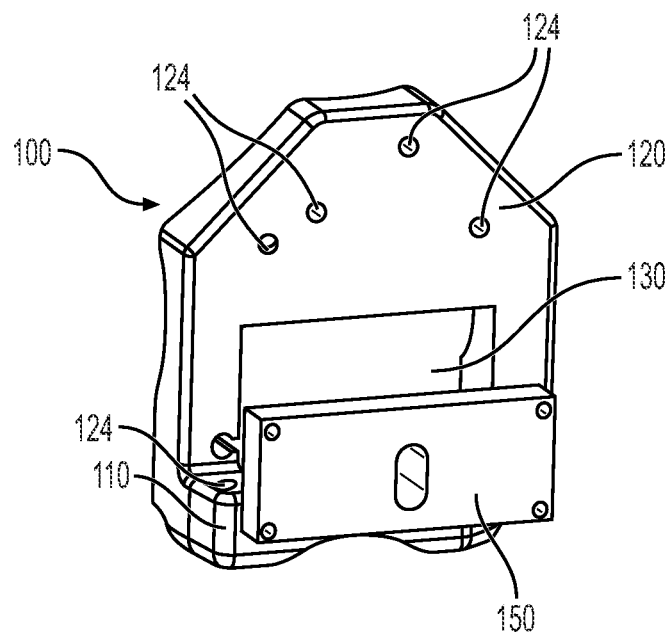

One embodiment of the alignment guide 100 is configured such that after resection of the tibia of the patient, a portion of or the entire tibial component 120 may be removed. FIGS. 9A-9C show a removable tibial cutting guide 150. The removable tibial cutting guide 150 is inserted into the opening 130 in the tibial component 120. The alignment guide 100 ensures that the cutting guide 150 is maintained in the proper location throughout the procedure, and that the location can be reproduced at a later time if desired. Once the cutting, sawing, or other procedure requiring the cutting guide 150 is complete, the cutting guide 150 is removable as shown in FIGS. 9B and 9C to allow for visualization of the bone, joint and talar component, and provide access to the talar component to insert a talar cutting guide if desired. The removable cutting guide 150 can be attached to the alignment guide 100 through the use of screws within holes 152 that were previously drilled into the cutting guide 150 and the alignment guide 100. The holes can be drilled based on the computer-based model so that the cutting guide 150 is automatically placed in the correct location in relation to the bone when the tibial surface is placed against the bone. Other known methods of attaching two components together, so that their positioning with respect to each other remains constant, may also be used. Examples of such connections include, friction fit, snap fit, the use of wires, or other tying devices, etc.

Figure 10A:
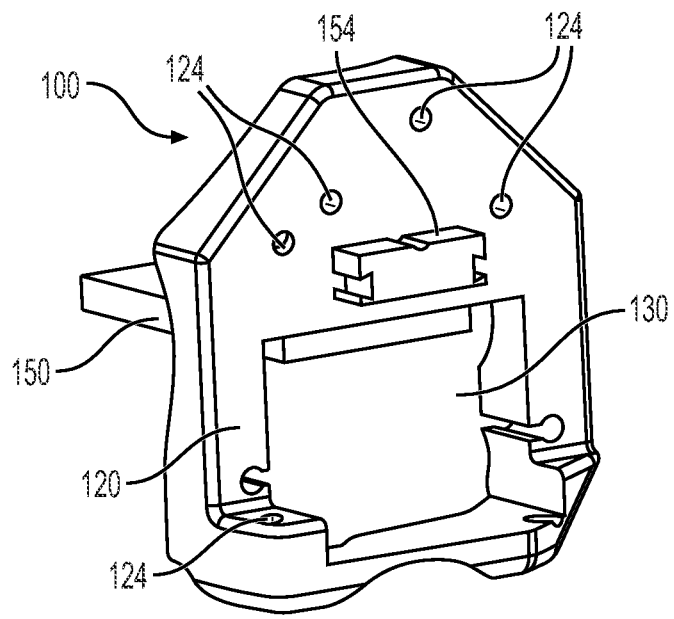
FIG. 10A is a computer-generated image of a perspective view of the front of the alignment guide of FIG. 6A having a different removable cutting guide than shown in FIG. 9A.
Figure 10B:
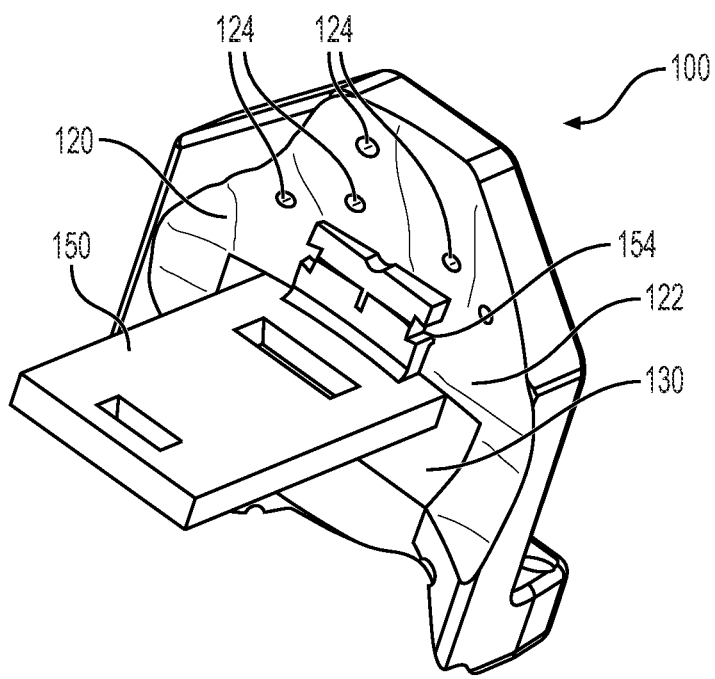
FIG. 10B is a perspective view of the back of the alignment guide of FIG. 10A.

FIGS. 10A and 10B show an alternate embodiment of a removable tibial cutting guide 150 in which the connection between the cutting guide 150 and the alignment guide 100 is different than that shown in FIG. 9A. In this figure, the removable cutting guide 150 is inserted within a slot 154 that is formed in the tibial component. The cutting guide 150 can be formed such that it snaps into the slot and can be pulled out of the slot when its use is no longer desired.

Removing the tibial cutting guide 150, or other component may expose the underlying bone for visualization or may allow the talar component to be attached or allow another guide, such as a talar cutting guide (not shown) to be located in the talar component 110 that may be used to resect a portion of the talus. A cutting or other guide in the talar component 110 may be similar to the guide 126 of the tibial component 120 in that the guide in the talar component is used to guide a tool used to remove or resurface talar bone. In a preferred embodiment such a guide in the talar component 110 may have one or more apertures that correspond to one or more prongs or other protrusions on the implant. The apertures can be used to drill holes, or otherwise remove portions of the bone that will allow the prongs or other protrusions on the implant to be inserted into and secured within the talus of the patient.

Figure 11C:
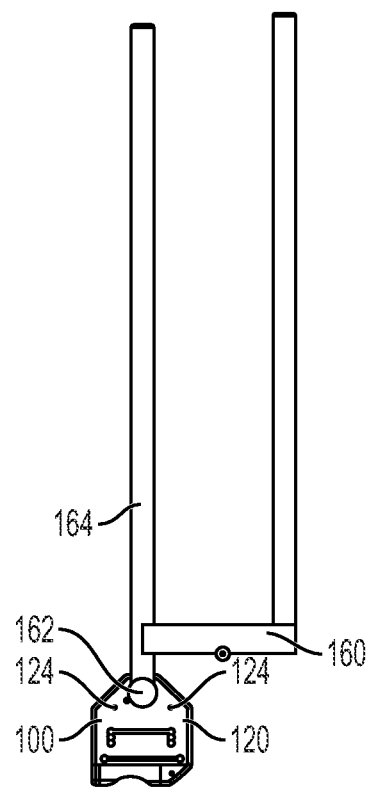
FIG. 11C is a perspective view of the alignment guide of FIG. 11A.

FIGS. 11A-11C show an alignment apparatus 160 that has been attached to the tibial component 120. Although the alignment guide 100 should always be in the correct position when the surfaces are in contact with the bones of the joint, it may be helpful to have a visual confirmation of the correct positioning. The alignment apparatus 160 of FIG. 11 may be attached to any part of the alignment guide 100 so long as the attachment is sufficiently secure to maintain the relative of the alignment apparatus 160 position with respect to the alignment guide 100 so that it can be used to verify the position of the alignment guide 100 through visual comparison with another part of the patient's anatomy.

Figure 11C:
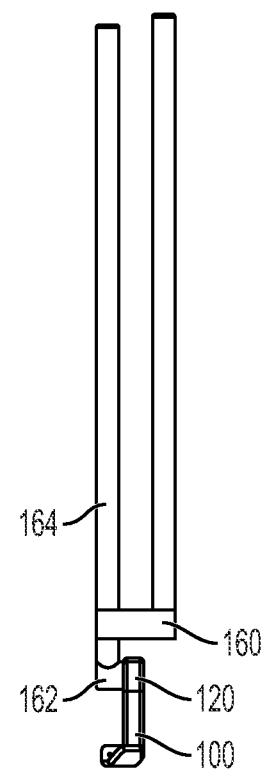
Figure 11C:
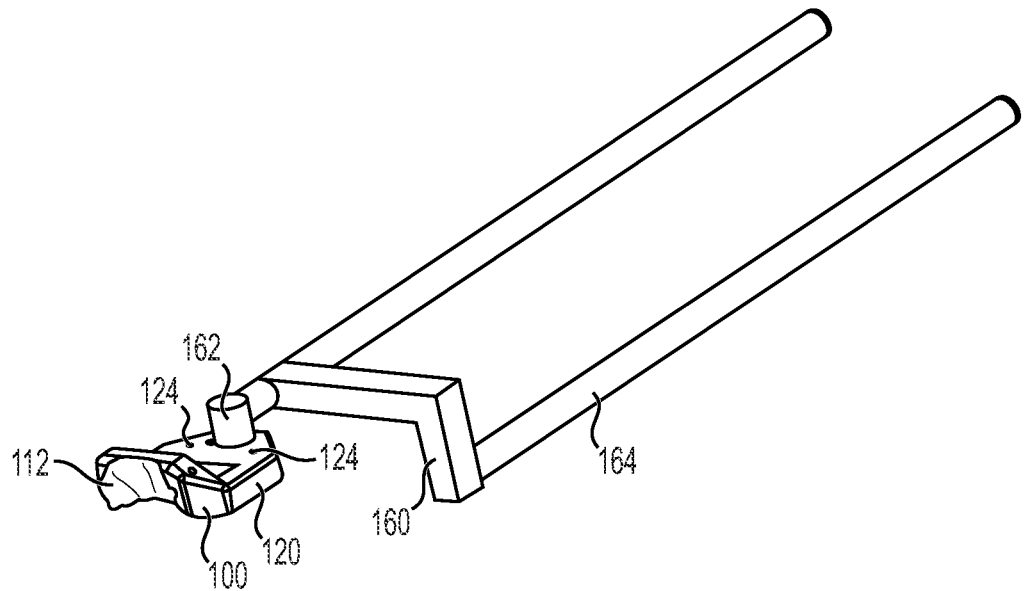

For example, the alignment apparatus 160 shown in FIGS. 11A-11C is attached to the tibial component 120 through the use of a screw 162 that is inserted within a hole in the alignment guide 100. The screw may be easily tightened by hand so that it is easy to attach and remove the apparatus 160 from the guide 100. Other similar securing methods, such as friction fit, hook and loop fasteners, tape, clamps, etc. ma be used for this purpose. In FIG. 11, the extensions 164 of the alignment apparatus 160 are compared to the longitudinal axis of the tibia to verify the position of the alignment guide 100.

A second embodiment of the present invention is a method of providing an alignment guide 100 for use in a total ankle replacement procedure. The method utilizes data obtained by imaging a patient's ankle when positioned in a preselected position. This image-based data may be obtained using any suitable, known imaging technology, such as MRI, CT, LCT, X-ray, etc. Three-dimensional modeling of the bone images from two-dimensional CT, MRI, or LCT image data can be accomplished using, for example, commercially available software. For example, medical imaging data from CT, or MRI or LCT scanners can be segmented to create accurate, patient specific three-dimensional models in STL or other similar format files. The STL file format is native to stereolithography CAD (Computer-Aided Design) software and can be used for rapid prototyping and computer-aided manufacturing. A related file format is AMF (Additive Manufacturing File Format), which can Support color and multiple materials. The STL or AMF files can be also converted to IGES (Initial Graphics Exchange Specification) files or other similar file formats that are neutral data formats, for example, to allow this digital exchange of information among different CAD software systems.

A computer-based model of the patient's ankle is created to replicate the patient's ankle positioned in a preselected position. The computer-based model is preferably a three-dimensional model, but may also be a series of two-dimensional images, or any other rendering made possible by using computer technology. The model may then be used to create the alignment guide 100 having the tibial component 120 and the talar component 110. Although the computer-based model is as exact a replica, or as close an approximation of the ankle of the patient in a preselected position, that the state of the technology in the art for imaging will allow, there are certain instances where modification of the image-based data, or the computer-based model is desired prior to the creation of the alignment guide 100. Such instances include, but are not limited to, correcting the data to compensate for either a chronic or acute injury that occurred to the patient's ankle at some time in the past. Alterations of the model may also be employed to correct alignment issues that may be present in the patient's ankle due to bone deformities, or bone degradation from disease. The model may be altered by alteration of the obtained image data to provide a desired shape of the patient's talus and/or tibia or by alteration of the model of the patient's ankle after it has been created from the originally obtained image data of the patient's ankle.

Alteration of the image data or the computer-based model can be used to compensate for injury, disease or damage to the patient's ankle in the ankle replacement procedure. Such compensation will involve one or more changes in the fabricated alignment guide 100 that will result from alteration of the model of the patient's ankle prior to fabrication of the alignment guide 100. Such changes may include changes in the surface portions 112, 222 of the talar and tibial components 110, 120 to match altered surface sections of the model of the patient's talus and tibia, changes in one or more guides provided in the alignment guide 100 for tools used to resect one or both of the patient's talus and tibia or for resurfacing a section of the surface of the patient's talus or tibia prior to inserting the implant, as well as providing corrective measures to ensure proper alignment replacement joint elements that may provide improved ankle motion and use.

This is an important feature of the invention since it allows the alignment guide 100 to be specially fabricated for a desired future configuration of the patient's ankle to be used in the ankle replacement. As a result, the present invention facilitates implementation of desirable corrective measures as part of the ankle replacement procedure to thereby potentially improve the patient's mobility and ensure a successful and reliable implantation of the total ankle replacement.

The tibial component 120 is created using the computer-based model by forming a surface portion 122 of the tibial component 120 that interfaces with a distal surface of at least a section of the model of the tibia of the ankle of the patient. Similarly, the talar component 110 of the alignment guide 100 is created using the computer-based model by forming a surface portion 112 of the talar component 110 that interfaces with a corresponding surface of a superior aspect of at least a section of the model of the talus body or talus neck of the ankle of the patient. The tibial component 120 and the talar component 110 are preferably integral to provide a one-piece alignment guide 100. Such an alignment guide 100 may be provided by 3D printing methods.

The optional third component of alignment guide 100, namely the navicular and cuboid component 140 can be fabricated in a similar fashion as the tibial and talar components 110, 120 utilizing the original or altered computer-based model of the patient's ankle. The navicular and cuboid component of the alignment guide 100 may have a surface that interfaces with a superior aspect of at least a section of either or both of the navicular and cuboid bones of the ankle of the patient that was modeled.

The method of creating the alignment guide 100 may also provide either or both of the tibial component 120 and the talar component 110 having a one or more apertures for guiding a drill, saw, or burring instrument. The method may also include providing wires, pins, or screws to hold the alignment guide 100 in place on the ankle of the patient during use.

The method of forming the tibial component 120 may also include configuring the tibial component 120 to allow visualization of one or both of a part of the tibia and the space between the tibia and the talus within the ankle joint. This visualization can be made to occur when the surface of the tibial component 120 is positioned in contact with the distal surface of the tibia. The area for visualization may include an aperture, or a removable component that may be removed during the surgical procedure at a time when viewing the talus, tibia, or space between the talus and the tibia might be necessary.

Another embodiment of the invention is a method of total ankle replacement in a patient. The method utilizes any embodiment of the alignment guide 100 as described herein. In this method, the distal surface of the tibia of the patient is exposed. A section of the superior part of the body and neck of the talus of the patient is also exposed. Once these surfaces of the bones are exposed, alignment guide 100 is located in place on the patient's ankle by positioning the surface portion 122 of the tibial component 120 against the exposed section of the distal surface of the tibia and positioning the surface portion 112 of the talar component 110 against the exposed section of the surface of the superior part of the body and neck of the talus. Once the surface portions 122, 112 of the tibial component 120 and the talar component 110 are placed in the correct location and the alignment guide 100 is secured to the patient's ankle, the ankle is held in its preselected position.

To help secure the alignment guide 100 during the surgical procedure, it can be affixed to one or both of the tibia or talus through the use of wires, pins, screws or other fastening device that is known in the art to secure a device to a bone.

Once the alignment guide 100 is secured to the bone, a cutting, drilling, or burring jig may be attached to the tibial or the talus component. The jig can be used to provide a guide for a cutting, drilling or burring devices to resect the correct portion of the bone for the total ankle replacement.

The tibia may be resected first using the alignment guide 100. Once the tibial component 120 has been used to properly resect the proper part of the tibia, a portion of the tibial component 120 of the guide may be removed to allow visualization of one or both of a part of the tibia and a space between the tibia and the talus when the surface of the tibial component 120 is in contact with the tibia. The portion of the tibial component 120 that is removed may be a small section, or may include almost the entire tibial component 120. It is desirable to leave a sufficient portion of the tibial component 120 in place such that the patient's ankle remains secured in its preselected position. After removal of a portion of the tibial component, the alignment guide 100 may be similar to the alignment guide 100 shown in FIGS. 6A and 6B.

The talar component 110 can be used to facilitate the provision of recesses in the talus. These recesses may be used to secure the replacement talar part of the total ankle replacement system. After the recesses are formed, the ankle replacement is secured to the tibia and talus of the patient. A prosthetic ankle having a talar component and a tibial component as described in U.S. Patent Application Publication No. 2016/0008139 can be used with the present alignment guide 100 as the TAR system.

The foregoing examples have been presented for the purpose of illustration and description and are not to be construed as limiting the scope of the invention in any way. The scope of the invention is to be determined from the claims appended hereto.

What is claimed is:
1. An alignment guide comprising:
   a. a talar component having a surface portion that interfaces with a corresponding surface of a superior aspect of at least a section of a talus body or talus neck of an ankle of a patient;
   b. a tibial component attached to the talar component having a surface portion that interfaces with a corresponding distal surface of at least a section of a tibia of the ankle of the patient; and
   c. a navicular and cuboid component attached to or integral with the talar component and having a surface that is configured to interface with a superior part of a section of a surface of the navicular bone and is configured to interface with a section of a surface of a cuboid bone of the patient; and
   wherein a combination of the talar component, and the tibial component is configured such that when the surface portion of the talar component is positioned in contact with the corresponding surface of the superior aspect of at least said section of the talus body or talus neck of the ankle of the patient, and the surface portion of the tibial component is positioned in contact with at the corresponding distal surface of at least said section of the tibia of the ankle of the patient, the ankle of the patient is positioned in a preselected position.

2. The alignment guide according to claim 1, further comprising means associated with at least one of the tibial component and the talar component for attaching one or more of a cutting, drilling and/or burring jig to the alignment guide.

3. The alignment guide according to claim 1
   a. wherein the talar component and the tibial component are integral with one another.

4. The alignment guide according to claim 1, wherein the surface portion of the talar component is made using image data of the surface of the superior aspect of at least said section of the talus body or talus neck of the ankle of the patient and the surface portion of the tibial component is made using image data of the distal surface of at least said section of the tibia of the ankle of the patient.

5. The alignment guide according to claim 4, wherein the image data is obtained with the patient's ankle in a preselected position.

6. The alignment guide according to claim 5, further comprising an attachment means for attaching the talar component to the tibial component, and
   wherein the image data is used to configure the attachment means to ensure that the ankle of the patient is positioned in a preselected position when:
   a) the talar and tibial components are attached to each other by the attachment means,
   b) the surface portion of the talar component is positioned in contact with the corresponding surface of the superior aspect of at least said section of the talus body or talus neck of the ankle of the patient, and
   c) the surface portion of the tibial component is positioned in contact with the corresponding distal surface of at least said section of the tibia of the ankle of the patient.

7. The alignment guide according to claim 6, wherein the attachment means is a releasable attachment means.

8. The alignment guide according to claim 1, wherein the tibial component comprises a removable section that, upon removal, allows visualization of one or both of a part of the tibia and a space between the tibia and the talus, when the surface portion of the tibial component is positioned in contact with the corresponding distal surface of at least said section the tibia.

9. The alignment guide according to claim 1, wherein the tibial component is configured to allow visualization of one or both of a part of the tibia and a space between the tibia and the talus, when the surface portion of the tibial component is positioned in contact with the corresponding distal surface of at least said section of the tibia.

10. The alignment guide according to claim 1, further comprising wires, pins or screws for attaching the alignment guide to the tibia and to the talus.

11. The alignment guide according to claim 1, wherein at least one of the tibial component and the talar component further comprises at least one aperture therein which is configured for guiding a drill, saw, or burring instrument.

12. A method comprising steps of:
   a. obtaining image-based data of a patient's ankle in a preselected position;
   b. producing a computer-based model of at least a portion of the patient's ankle in a preselected position from the image-based data;
   c. creating a tibial component for the alignment guide using the computer-based model including forming a surface portion of the tibial component that interfaces with a distal surface of at least a section of a tibia of the ankle of the patient;
   creating a talar component for the alignment guide using the computer-based model including forming a surface portion of the talar component that interfaces with a corresponding surface of a superior aspect of at least a section of a talus body or talus neck of the ankle of the patient;
   creating a navicular and cuboid component having a surface portion that interfaces with a corresponding surface of a superior aspect of at least a section of navicular and cuboid bones of the ankle of the patient, and
   securing the navicular and cuboid component to the talar component; and
   wherein the tibial component and the talar component are configured such that when the surface portion of the talar component is positioned in contact with the corresponding surface of the superior aspect of at least said section of the talus body or talus neck of the ankle of the patient, and the surface portion of the tibial component is positioned in contact with the distal surface of at least said section of the tibia of the ankle of the patient, the ankle of the patient is positioned in the preselected position.

13. The method of claim 12, further comprising steps of
   affixing the alignment guide to one or both of the tibia and talus of the ankle of the patient using wires, pins, or screws,
   attaching a cutting, drilling or burring jig to the tibial component of the alignment guide; and
   resecting bone using the cutting, drilling, or burring jig.

14. The method of claim 12, further comprising steps of removing a portion of the tibial component to allow visualization of one or both of a part of the tibia and a space between the tibia and the talus, when the surface portion of the tibial component is positioned in contact with the corresponding distal surface of at least said section of the tibia of the ankle of the patient, and
   creating recesses in the talus of the patient using a guide which forms part of the talar component.

* * * * *